US005578468A

United States Patent [19]

Pickup et al.

[11] Patent Number: 5,578,468
[45] Date of Patent: Nov. 26, 1996

[54] SITE-SPECIFIC RNA CLEAVAGE

[75] Inventors: David J. Pickup, Cary; Dhavalkumar Patel; James B. Antczak, both of Durham, all of N.C.

[73] Assignee: Duke University, Durham, N.C.

[21] Appl. No.: 113,646

[22] Filed: Aug. 31, 1993

Related U.S. Application Data

[63] Continuation-in-part of Ser. No. 84,406, Aug. 10, 1987, Pat. No. 5,443,964.

[51] Int. Cl.$^6$ .............................. C12N 15/10; C12N 15/11; C12N 5/10; C12N 1/21
[52] U.S. Cl. .................. 435/91.32; 536/24.1; 536/23.1; 435/240.1; 435/240.2; 435/252.3; 435/235.1; 935/3; 935/6
[58] Field of Search .................. 536/24.1; 435/320.1, 435/240.1, 240.2, 91.1, 91.32, 91.33, 235.1; 935/3, 6, 34, 36

[56] References Cited

U.S. PATENT DOCUMENTS

| | | | |
|---|---|---|---|
| 4,419,446 | 12/1983 | Howley et al. | 435/69.1 |
| 4,495,190 | 1/1985 | Hagberg et al. | 514/262 |
| 4,495,280 | 1/1985 | Bujard et al. | 435/6 |
| 4,503,142 | 3/1985 | Berman et al. | 435/6 |
| 4,508,826 | 4/1985 | Foor et al. | 435/320.1 |
| 4,510,245 | 4/1985 | Cousens et al. | 435/172.3 |
| 4,511,502 | 4/1985 | Builder et al. | 530/417 |
| 4,511,503 | 4/1985 | Olson et al. | 530/422 |
| 4,511,652 | 4/1985 | Fogel et al. | 435/29 |
| 4,512,922 | 4/1985 | Jones et al. | 530/408 |
| 4,514,497 | 4/1985 | Kit et al. | 435/235.1 |
| 4,517,294 | 5/1985 | Bock et al. | 435/69.4 |
| 4,518,526 | 5/1985 | Olson | 530/351 |
| 4,518,584 | 5/1985 | Mark et al. | 424/85.2 |
| 4,518,690 | 5/1985 | Guntaka | 435/69.4 |
| 4,554,159 | 11/1985 | Roizman et al. | 424/205.1 |
| 4,603,112 | 7/1986 | Paoletti et al. | 435/235.1 |
| 4,745,051 | 5/1988 | Smith et al. | 435/69.51 |
| 5,364,773 | 11/1994 | Paoletti et al. | 435/235.1 |

FOREIGN PATENT DOCUMENTS

| | | |
|---|---|---|
| 0127839 | 12/1984 | European Pat. Off. . |
| 0155476 | 9/1985 | European Pat. Off. . |
| 0198328 | 10/1986 | European Pat. Off. . |
| 1202288 | 8/1989 | Japan ............................ C12N 15/00 |
| 2105344 | 3/1983 | United Kingdom . |
| 8402077 | 6/1984 | WIPO . |

OTHER PUBLICATIONS

"Improvement of the 5' upper region of the poxvirus A-type inclusion (ATI) gene and improvement of alien gene manifest vectors by the 3' lower region of said gene" [English translation of JP 1-202288].
Antczak, J. B. et al. 1992. Proc. Natl. Acad. Sci. USA vol. 89 pp. 12033–12037.
Patel, D. D. et al. 1988. Proc. Natl. Acad. Sci. USA vol. 85 pp. 9431–9435.
Simonsen et al, "Analysis of Process and Polyadenylation Signals of the Hepatitis B Virus Surface Antigen Gene by Using Simian Virus 40–Hepatitis B Virus Chimeric Plasmids", Molecular and Cellular Biology 3(12):2250–2258 (1983).
Antczak et al, "Site-specific RNA cleavage generates the 3' end of a proxvirus late mRNA", Proc. Natl. Acad. Sci. USA 89:12033–12037 (1992).
Patel et al, "Messenger RNAs of a strongly-expressed late gene of cowpox virus contain 5'-terminal poly(A) sequences", EMBO Journal 6:3787–3794 (1987).
Boyle et al, "Virus Research" 10:343–356 (1988).
Esposito et al, Virology 165:313–316 (1988).
Pickup et al, "Hemorrhage in lesions caused by cowpox virus is induced by a viral protein that is related to plasma protein inhibitors of serine proteases", Proc. Natl. Acad. Sci. USA 83:7698–7702 (1986).
"Pouwels, eds in Cloning vectors" VIII Bbi 15.
Patel et al, Virology 149:174–189 (1986).

*Primary Examiner*—Mary E. Mosher
*Attorney, Agent, or Firm*—Nixon & Vanderhye P.C.

[57] ABSTRACT

The present invention relates to a method of effecting site-specific cleavage of RNA and to an element and a factor responsible for such cleavage.

9 Claims, 10 Drawing Sheets

```
                    -15              ↓                +15
Primary RNA    5'-CACAAAAGAUUUUAUCCGAUAAUUCUUCAU-3' mRNA 3' end    5'-CACAAAAGAUUUUAUAAAAAAAAAAAAAAA(n)
```

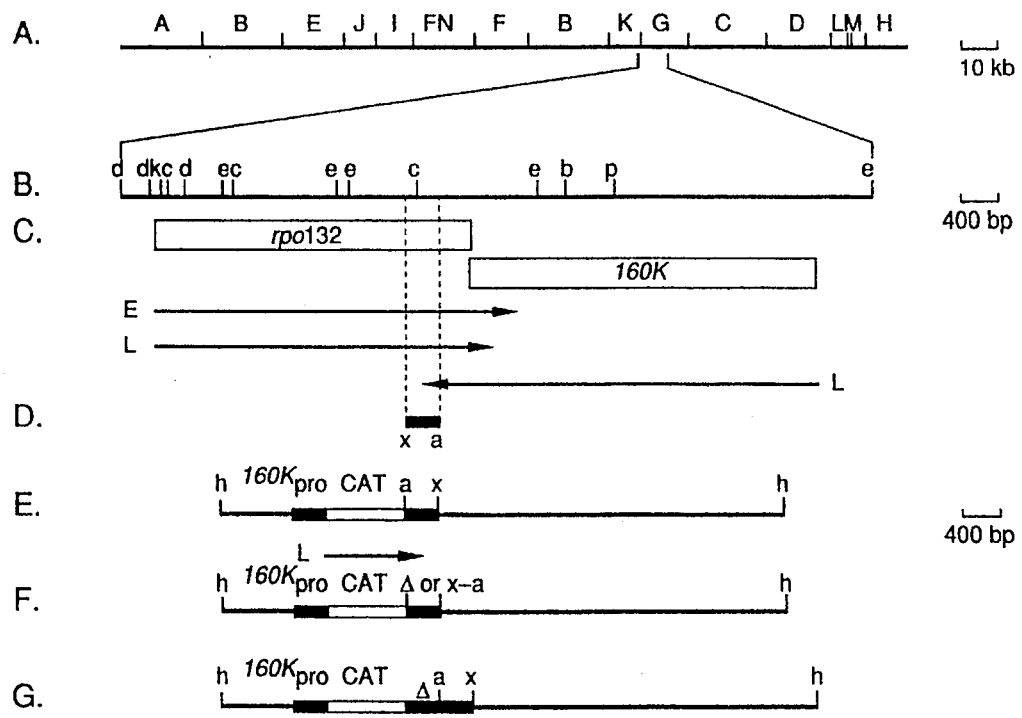

FIG. 9

```
Alu I
    -151
AGCTTCGTCTTTTTACCTCTACATCTAACGGTTGCCTTGTCCTGAGTTAAATGCCTCA
                                                     -50
GACGCAAGTAATAAATTGGTCCAAAAAATACTTTGGATGCATAAGGCTTATCCGTTTC
     -25         -15              -1
AGGATCATAGAATCTTTTCACAAAAGATTTTATCCGATAATTCTTCATCAGACAAT
                              -2      +10      +20

TTCGGATTTGAATGCTCATAACATTGTTTAGCGAATTGCATATATGTATCGATGGATG
        +38              +56                +72

TTTCGTTACTACTAGGAAAACAGACAGGTCGGTTTTCTCCCTTATTGTTGTACGGCTT

AGCAGAATATGCGGCTGTTAAAATAACTTCTATCAACATAGATATAGTTTTCTAGA
                                                   +196
                                                   Xba I
```

FIG. 10

A. Sequence of the RNA containing the AX element

```
 -15              -1                                       +38
   CACAAAAGAUUUUAUCCGAUAAUUCUUCAUCAGACAAUUUCGGAUUUGAAUGC
```

B. Additional 5' and 3' deletion mutations

```
   -10 AAGAUUUUAUCCGAUAAUUCUUCAUCAGACAAUUUCGGAUUUGAAUGC
         -5 UUUUAUCCGAUAAUUCUUCAUCAGACAAUUUCGGAUUUGAAUGC
   CACAAAAGAUUUUAUCCGAUAAUUCUUCAUCAGACAAUUUCGGAUUUGAA +35
   CACAAAAGAUUUUAUCCGAUAAUUCUUCAUCAGACAAUUUCGGAU +30
   CACAAAAGAUUUUAUCCGAUAAUUCUUCAUCAGACAAUUU +25
```

C. Linker scanning mutations of the AX element

```
  -15  -10  -5  -1   +5  +10  +15  +20  +25  +30  +35 +38
    CACAAAAGAUUUUAUGUACAAAUUCUUCAUCAGACAAUUUCGGAUUUGAAUGC
    CACAAAAGAUUUUAUCCGAUGUACAUUCAUCAGACAAUUUCGGAUUUGAAUGC
    CACAAAAGAUUUUAUCCGAUAAUUCGUACACAGACAAUUUCGGAUUUGAAUGC
    CACAAAAGAUUUUAUCCGAUAAUUCUUCAUGUACAAAUUUCGGAUUUGAAUGC
    CACAAAAGAUUUUAUCCGAUAAUUCUUCAUCAGACGUACACGGAUUUGAAUGC
    CACAAAAGAUUUUAUCCGAUAAUUCUUCAUCAGACAAUUUGUACAUUGAAUGC
```

D. Components of the AX element whose complete or partial substitution either abolishes or severely reduces the efficiency with which the AX element is cleaved in cells

```
  -15          -5  -1   +5                   +26       +35
   ---------UUUAUCCGAU------------------CGGAUUUGAA---
```

FIG. 13

SITE-SPECIFIC RNA CLEAVAGE

This invention was made with support under Grant Nos. R01 AI23886 and 5T32CA09111 awarded by the National Institutes of Health. The U.S. Government has certain rights in this invention.

This is a continuation-in-part of application Ser. No. 07/084,406, filed Aug. 10, 1987, now U.S. Pat. No. 5,443,964 the entire contents of that application being incorporated herein by reference.

FIELD OF THE INVENTION

The present invention relates to a method of effecting site-specific cleavage of RNA and to an element and a factor responsible for such cleavage.

BACKGROUND

The 3' ends of mRNAs are formed in eukaryotic cells either by the post-transcriptional processing of a primary RNA, or, less commonly, by the termination of transcription (Proudfoot et al, Transcription and Splicing, Eds Hames and Glover, IRL Press Limited (Oxford), pp. 97–99 (1988); Wickens, Trends Biochem. Sci., 15:277 (1990)). The 3' ends of the mRNAs of DNA viruses of most types are formed in a similar way, because most viruses employ the transcriptional apparatus of the cell to synthesize viral mRNAs.

The poxviruses differ from other DNA viruses in that they replicate in the cytoplasm of the cell, employing numerous viral enzymes, instead of host cell enzymes, to synthesize their RNAs. Poxviral proteins known to be involved in RNA synthesis and processing include a multisubunit RNA polymerase that resembles eukaryotic RNA polymerase II, several transcription factors, a capping-enzyme complex, an RNA methyltransferase, a poly(A) polymerase, and an endoribonuclease (Moss, Virology, Eds. Fields and Knipe, Raven Press (New York), pp. 2079–2112 (1990)). This assemblage of viral proteins suggests that the poxvirus may encode all the factors necessary for viral RNA synthesis, including those required for RNA 3' end formation.

The transcription of poxvirus genes is a temporally regulated process. Early genes are transcribed before viral DNA replication, intermediate genes are transcribed after the onset of viral DNA replication, and late genes are transcribed after the expression of the intermediate genes (Moss, Annual Rev. Biochem., 59:661 (1990)).

The processes used to form the 3' ends of viral RNAs are temporally regulated also. The 3' ends of the early RNAs are generated by the termination of transcription, which occurs about 50 nucleotides downstream of the signal sequence 5'UUUUUNU3' in the nascent RNA (Rohrmann et al, Cell, 46:1029 (1986); Shuman et al, J. Biol. Chem., 263:6220 (1988)). Interestingly, the process generating the termination of transcription of early genes does not appear to operate after the onset of viral DNA replication (Weir et al, J. Virol., 51:662 (1984); Weinrich et al, J. Virol., 61:639 (1987); Vos et al, EMBO J., 10:2553 (1991)). RNA transcripts of most characterized late genes appear to be heterogeneous in length, lacking the defined 3' ends characteristic of the early mRNAs (Mahr, et al, J. Virol., 49:510 (1984); Cooper et al, J. Virol., 37:284 (1981)). However, a few late transcription units whose RNAs are homogeneous in length have been identified. These include the cowpox virus gene encoding the most abundant viral protein, the major protein component of the A-type inclusion (ATI) bodies (hereinafter referred to as the ATI gene or 160K gene) (Patel et al, EMBO J., 6:3787 (1987); Patel et al, Virology, 149:174 (1986)); the equivalent vaccinia virus gene (hereinafter also referred to as the 94K gene) (Patel et al, Proc. Natl. Acad. Sci., 85: 9431 (1988); Amegadzie et al, Virology, 186:777 (1992)); and the telomeric transcription units of vaccinia virus, cowpox virus, and raccoon pox virus (Parsons et al, Virology, 175:69 (1990)).

Prior to the present invention, the mechanism involved in the generation of the defined 3' ends of late viral RNAs was not known. It has now been demonstrated that specific elements governing late transcription of poxvirus DNA can be used to direct RNA 3' end formation by site-specific RNA cleavage. In particular, it has now been demonstrated that the 3' ends of the late RNAs encoding the ATI protein are generated, not by the termination of transcription, as is the case for 3' end formation of early RNAs, but by site-specific cleavage of a precursor RNA transcript. This site-specific cleavage is effected by a poxvirus-induced factor, which factor forms part of the present invention.

The present invention makes possible site-specific RNA cleavage either in vitro or in vivo. In addition, the factor of the invention can be used in conjunction with other RNA processing enzymes to generate novel RNA molecules.

OBJECTS AND SUMMARY OF THE INVENTION

It is an object of the present invention to provide a method of effecting site-specific cleavage of RNA. It is a further object of the present invention to provide an element and a factor responsible for such cleavage and kits comprising same.

In one embodiment, the present invention relates to an isolated RNA fragment comprising an AX element.

In a further embodiment, the present invention relates to a construct comprising a non-A-type inclusion protein-encoding sequence operably linked to a promoter and to an AX element-encoding sequence.

In another embodiment, the present invention relates to an isolated factor that specifically cleaves an AX element.

In yet another embodiment, the present invention relates to a method of screening a sample for the presence of a factor that specifically cleaves an AX element. The method comprises:

i) contacting the sample with an RNA molecule comprising the AX element under conditions such that specific cleavage of the AX element can be effected by the factor; and ii) detecting the presence of products of that cleavage.

Further objects and advantages of the present invention will be clear from the description that follows.

BRIEF DESCRIPTION OF THE DRAWINGS

FIG. 9: Position of the 160K gene and the AX element in the cowpox virus genome. (A) KpnI restriction map of the genome of the Brighton Red (BR) strain of cowpox virus. (B) Restriction map of a 7.8 kb fragment of CPV-BR which overlaps the KpnI K-G junction. Restriction sites are abbreviated as follows: b, Bam HI; c, Cla I; d, Dra I; e, EcoRI; k, Kpn I; and p, Pst1. (C) Transcriptional map of the rpol32 and 160K genes. The rpol32 gene encodes the second largest subunit of the viral DNA-dependent RNA polymerase. The positions of the coding regions of the two genes are indicated by rectangles. The arrows represent the transcribed regions: "E" at early times after infection, and "L" at late times after infection. The tail of each arrow corresponds to the beginning of a transcribed region. Each arrowhead corresponds to the extent of complementarity between the defined 3'-ends of a transcript (when detectable) and the viral DNA. (D) A 347 bp Alu I-Xba I fragment (a x) contains the element designated AX that directs 3' end formation in RNAs of the 160K gene. (E-F) representative maps of the Hind IIIJ fragments of the genomes of the WR strain of vaccinia virus after these fragments have been modified to contain a copy of the bacterial chloramphenicol acetyltransferase (CAT) gene (under the transcriptional control of the late promoter of the 160K gene) inserted in the thymidine kinase gene. (E) The 347 bp Alu I-Xba I fragment containing the AX element is downstream of the CAT gene. (F) The 347 bp Alu I-Xba I fragment containing either 5' or 3' deletions of the AX element is downstream of the CAT gene. In one recombinant virus the 347 bp Alu I-Xba I fragment was placed in the opposite orientation to that in which it is found downstream of the 160K gene (x-a). (G) In one recombinant there was a partial duplication of the 347 bp Alu I-Xba I fragment such that the construct contained two copies of the AX element in tandem.

FIG. 10: Nucleotide sequence of the Alu I-Xba I fragment containing the AX element (CAE II); the sequence of the coding strand is shown. The vertical bar corresponds to the position of the cleavage in the RNA version of this fragment. Nucleotides are numbered with respect to the position of the cleavage site (i.e. nucleotides upstream of the cleavage site are numbered −1 to −151, and those downstream are numbered +1 to +196). The ends of the 5' and 3' deletions of this fragment are indicated (see also FIG. 13) (SEQ NO ID:18).

FIG. 13: (A) Sequence of the RNA containing the AX element as defined by the initial series of 5' and 3' deletion analyses (numbered as in FIG. 10) (SEQ ID NO:19). (B) Sequences of additional 5' and 3' deletions of this region (SEQ ID NO:20 to SEQ ID NO:24). (C) Sequences of the series of linker scanning mutations (underlined) made in the AX element (SEQ ID NO:25 to SEQ ID NO:30). (D) Summary of the components of the AX element whose deletion or partial substitution either abolishes or severely reduces the ability of the AX element to be cleaved in virus-infected cells. The underlined sequences are complementary. Nucleotides that can be substituted without major effect upon the ability of the AX element to be cleaved are indicated by a "−" (SEQ ID NO:31 and SEQ ID NO:32)

DETAILED DESCRIPTION

Application No. 07/084,406 describes modified viral nucleotide sequences and their use in directing expression of genes cloned into poxvirus-derived vectors. That application identifies the sequences as cis-acting elements (CAE-I and CAE-II) that control the transcription of the ATI gene (160K gene) of cowpox virus. CAE-II is indicated in Application No. 07/084,406 as being responsible for the production of distinct mRNA 3' ends when inserted downstream of the encoding gene.

Figure 2:
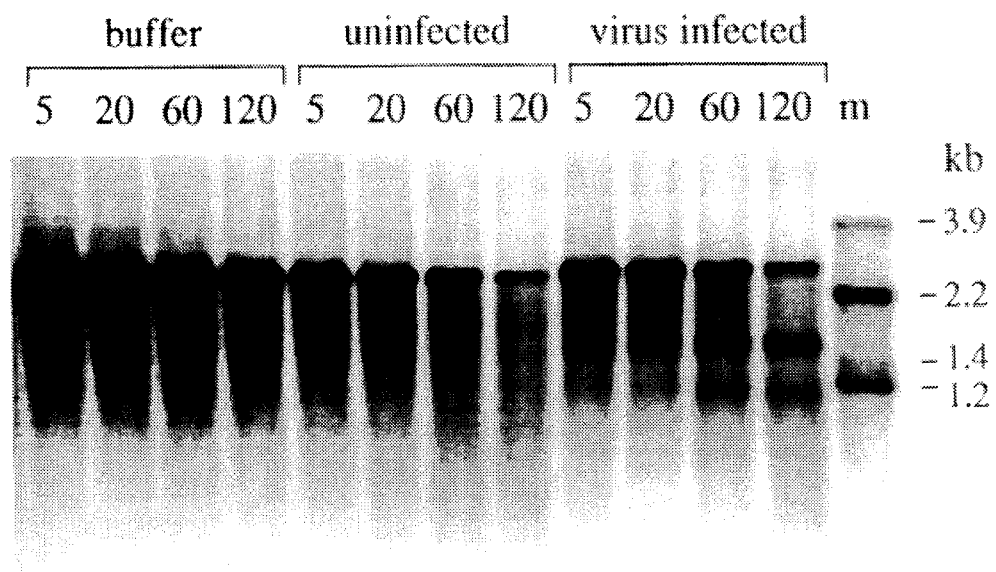
FIG. 2: RNA 3' end formation in vitro is dependent upon an activity present in extracts of virus-infected cells. $^{32}$P-labeled 2.7-kb RNAs transcribed from Nco I-linearized p2098 were incubated in reaction mixtures containing buffer alone, or buffer supplemented with extract of uninfected HeLa cells or with extract prepared from HeLa cells 15 hours after they had been infected with vaccinia virus. After incubation for 5, 20, 60 or 120 minutes, equal volumes were removed from each reaction mixture. RNAs were recovered from each sample and then resolved by agarose/formaldehyde gel electrophoresis. $^{32}$P-labeled RNAs were visualized by autoradiography. The incubation period is indicated above each lane; lane m contained single-stranded RNA standards.

FIG. 2 of Application No. 07/084,406 discloses the nucleotide sequence of the 347-bp AluI-XbaI fragments designated as CAE-II (see also FIG. 10 herein). As will be clear from the Examples that follow, the 3'-ends of the late mRNAs encoding the ATI protein are generated by site specific cleavage of a primary RNA transcript precisely after the sequence 5'-UUUUAU-3' (corresponding to positions 150 to 155 in above-referenced FIG. 2 of Application No. 07/084,406 and positions −6 to −1 in FIG. 10 herein), forming a new RNA 3'-end that is then polyadenylated. This cleavage site is within the cis-acting element that is designated hereinafter as the AX element.

Figure 11:
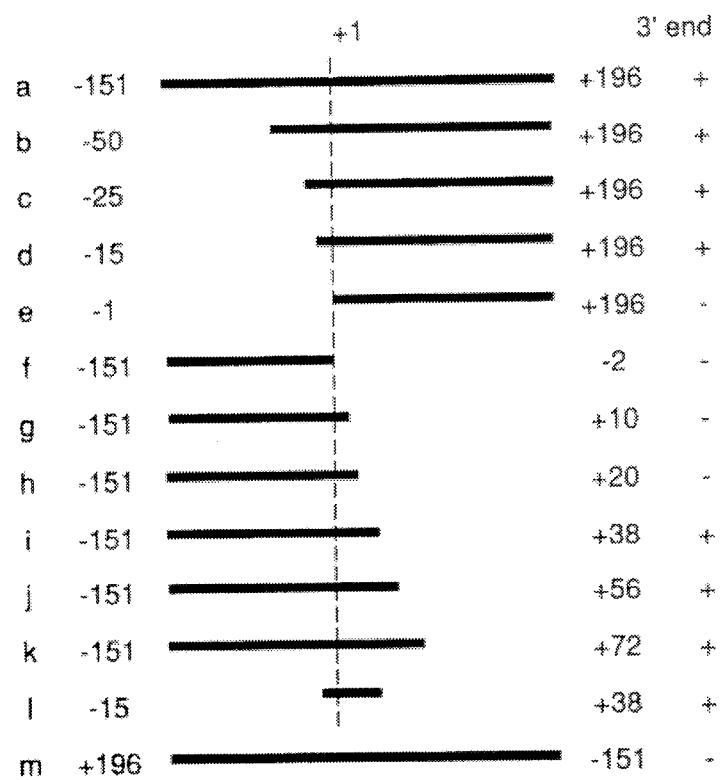
FIG. 11: Deletion analysis of the 347 nucleotide Alu I-Xba I fragment encoding the AX element. (a–m) Fragments of the Alu I-Xba I fragments were inserted into the genomes of vaccinia virus as described above (FIG. 9, part F and FIG. 10). The ability of each of these fragments to direct RNA cleavage within the AX element was determined by Northern blot analyses (FIG. 12), and scored as + or − 3' end. The vertical broken line corresponds to the position of the cleavage site (between nucleotides −1 and +1). (m) represents the full length 347 nucleotide Alu I-Xba I fragment inserted in the reverse orientation with regard to transcription extending through the CAT gene.
Figure 12:
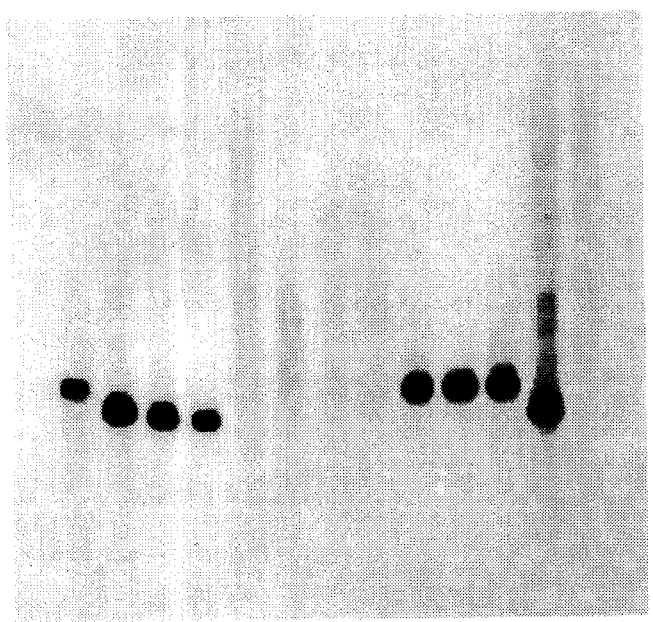
FIG. 12: Northern blot analyses of the CAT RNAs containing the variants of the 347 nucleotide Alu I-Xba I fragment. Recombinant vaccinia viruses were constructed, each containing a copy of the CAT gene under the transcriptional control of the promoter element of the 160K gene (FIG. 9, part F, FIG. 10, and FIG. 11). At late times after infection, polyadenylated RNAs extracted from cells infected with these viruses, were resolved by agarose gel electrophoresis, and then transferred to a nylon membrane. The immobilized RNAs were probed with single-stranded RNA probes specific for the coding region of the CAT gene. The viruses contained either: Lanes a–l, a CAT gene upstream of one copy of a deleted version of the Alu I-Xba Ia fragment (as per a–l in FIG. 11), in the same orientation in which it is found downstream of the 160K gene; Lane m, a CAT gene upstream of one copy of the Alu I-Xba I fragment in the opposite orientation to that in which it is found downstream of the 160K gene. The CAT transcripts that were cleaved are of defined lengths; these cleaved RNAs are visualized as discrete bands.

The AX element is localized in a 40 nucleotide region containing the above-referenced cleavage site. The majority of the element occurs downstream of the cleavage site. As will be clear from Example 4 below, 5' and 3' deletion analyses indicate that sequence information sufficient to effect 3' end formation is contained within the region between −15 and +38 relative to the 3' end site (ie, position −1 in FIG. 10). Indeed, a construct containing only this region of the Alu I-Xba I fragment is sufficient to effect 3' end formation (FIGS. 11 and 12, lane 1). The data presented in Example 5 demonstrate that the 5' boundary of the AX element lies between positions −5 and −1 (with reference to FIG. 10) and that the 3' boundary of the AX element lies between positions +30 and +35.

It will be evident from Example 5 that various substitutions can be made within the AX element. Data derived from linker scanning studies and from deletion analyses indicate that sequences close to the two boundaries of the AX element (i.e. −5 to +5 and +26 to +35, as shown in FIG. 13, D) contribute to the capacity of the AX element to be cleaved in cells. The linker scanning mutations indicate that the sequence between these two regions can be altered without preventing these altered elements from being cleaved. Thus, the AX element can be considered to comprise two sub-elements (see FIG. 13, D) separated by a sequence of about 20 nucleotides (the sequence and length of which can influence the efficiency of cleavage of the RNA element, but otherwise act as a secondary variable component of the complete element). The invention relates not only to the AX element and variants thereof specifically recited herein, but to variants of that element that permit cleavage. One skilled in the art will appreciate that other functional variants can be readily identified using linker-scanning mutations (see Example 5 below) and other methods of mutagenesis. One skilled in the art will also appreciate that variants may differ somewhat in their susceptibility to cleavage and in respect of the specific site at which they are cleaved.

Figure 14:
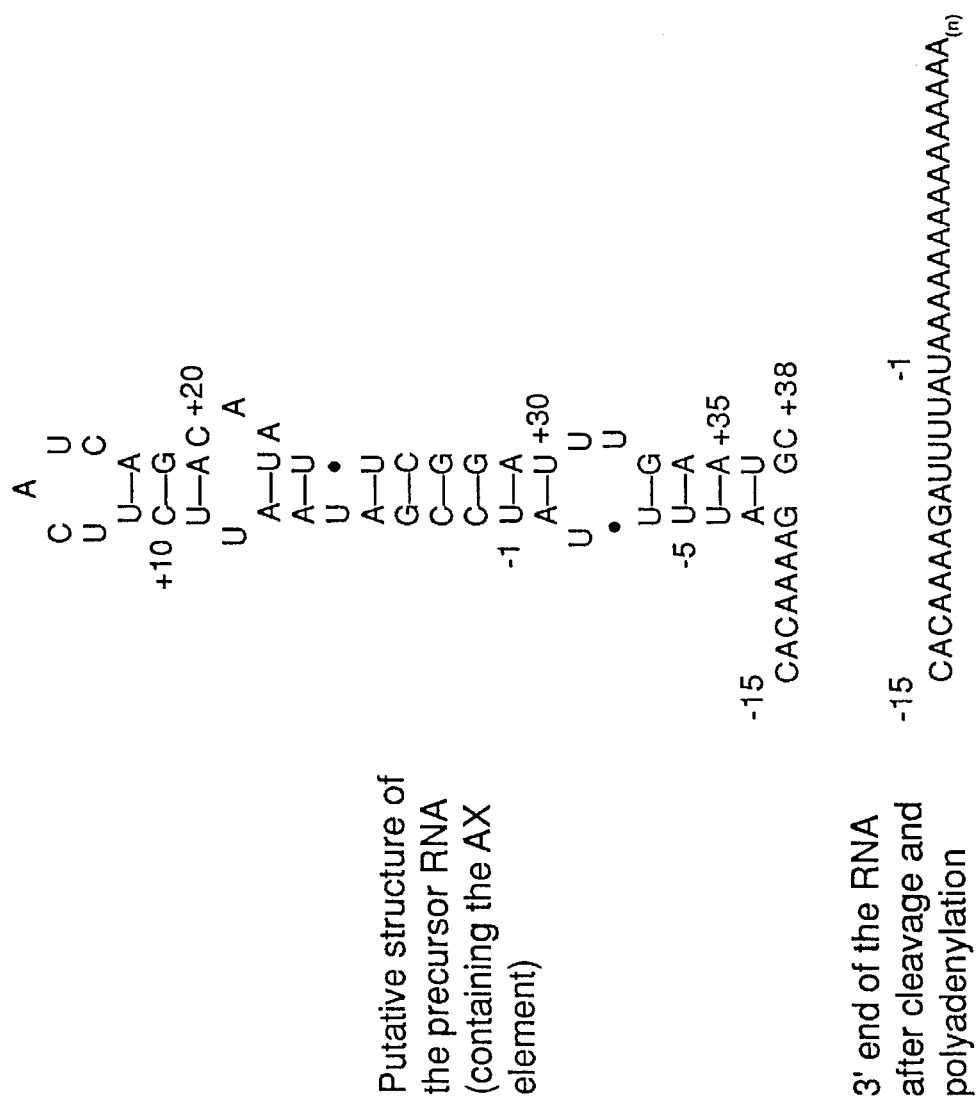
FIG. 14: A stem-loop structure that could form by basepairing within the uncleaved AX element in a precursor RNA (nucleotides numbered with respect to the RNA cleavage site). The lower line shows the sequence of the 3' end of a mature mRNA of the 160K gene. (SEQ ID NO: 34)

It is noteworthy that portions of the two flanking sub-elements underlined in FIG. 13, D are complementary, thus potentially allowing recognition of either a symmetrical nucleotide sequence, or an RNA structure generated by base-pairing between the two complementary portions of these sub-elements. An example of an RNA structure that can be generated in such a fashion is shown in FIG. 14. In this model, the two flanking sub-elements of the AX element form the stem of an RNA loop. The intervening sequence corresponds mainly to the loop portion of the structure. The present invention thus includes within its scope the AX element, whether that element is defined according to sequence or structure, or both.

The AX element can be used in an in vitro cleavage assay essentially as described by Antczak et al (Proc. Natl. Acad. Sci. USA 89:12033 (1992)) (and as described in Example 6). That is, protein fractions resolved, for example, by chromatographic procedures can be incubated with RNA containing the AX element (such as the 2.7 kb RNA described in Example 6) in order to determine which fractions contain the factor capable of cleaving the AX element (the RNA can be labeled, for example, with $^{32}$P, for purposes of detection). Site-specific cleavage of the RNA containing the AX element by factors present in these fractions can be assessed as described by Antczak et al (Proc. Natl. Acad. Sci. USA 89:12033 (1992)).

Figure 15:
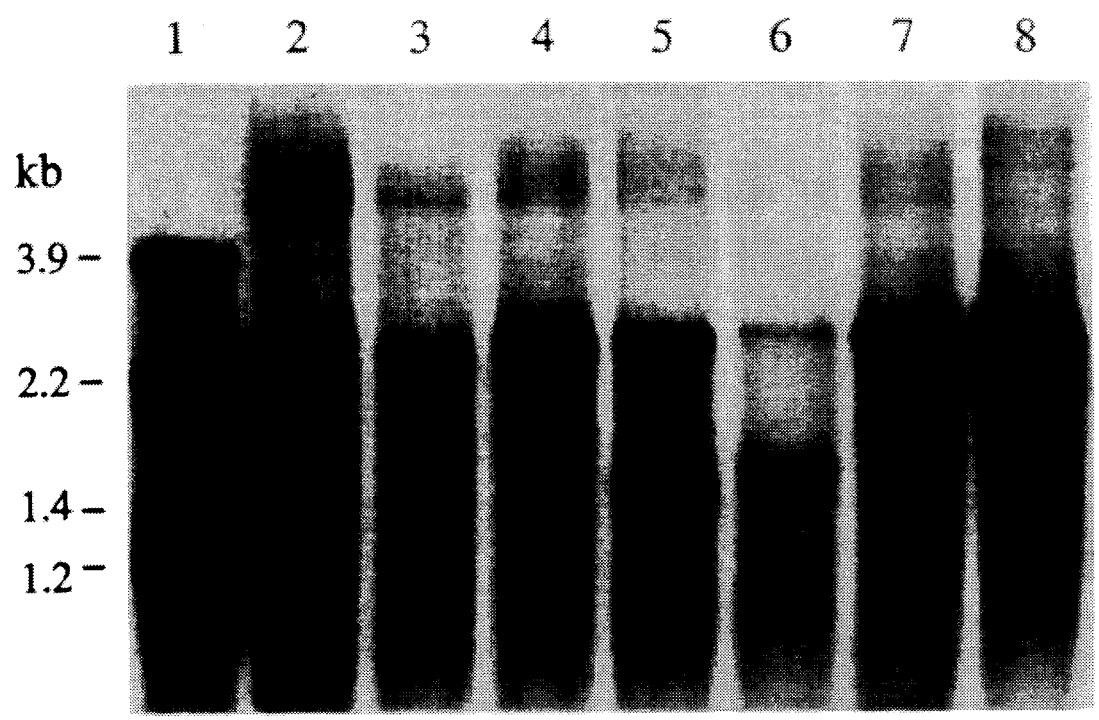
FIG. 15: Comparison of in vitro RNA cleavage activities in various cell or virus extracts. $^{32}$P-labeled 2.7 kb RNA was incubated for 120 min in reactions containing extracts from the sources indicated below. After incubation, RNA was extracted from each reaction and the reaction products were resolved by agarose-formaldehyde gel electrophoresis. The figure depicts an autoradiogram of the dried gel. Lane 1, $^{32}$P-labeled reovirus mRNA (to provide size markers). Lanes 2–7 contain RNA products of incubation of the 2.7 kb RNA in extracts obtained from: lane 2, uninfected HeLa cells; lane 3, HeLa cells, 2 hours after infection with vaccinia virus; lane 4, HeLa cells, 18 hours after infection with vaccinia virus; lane 6, L cells, 18 hours after infection with vaccinia virus; and lane 7, purified vaccinia virus particles. Lane 8, products of incubation of the 2.7 kb RNA in extract buffer alone.

The present invention relates, not only to the AX element but also to the factor responsible for effecting site-specific cleavage of that element, which factor can be identified using the assay system described above. In general, the factor can be defined by its ability to direct site-specific cleavage of an RNA containing an AX element. The factor can also direct site-specific cleavage of an RNA containing variants of the AX element when the variant elements are those that support cleavage in a cell, as described, for example, in FIGS. 9–12. The factor may also be able direct site-specific cleavage of an RNA-containing element structurally similar to the AX element but differing in sequence from the specific element described in the Examples that follow. The factor of the invention is detectable in extracts prepared as described by Antczak et al (Proc. Natl. Acad. Sci. USA 89:12033 (1992)) from HeLa cells that have been infected with vaccinia virus and it is detectable in extracts prepared as described by Antczak et al (Proc. Natl. Acad. Sci. USA 89:12033 (1992)) from L cells that have been infected with vaccinia virus (FIG. 15). The factor is not, however, detectable in extracts prepared as described by Antczak et al (Proc. Natl. Acad. Sci. USA 89:12033 (1992)) from either uninfected HeLa cells (FIG. 15, lane 2,) or (FIG. 15, lane 3) HeLa cells, 2 hours after infection (where there is a high degree of non-specific degradation of the 2.7 kb RNA, preventing determination of the presence or absence of the site-specific RNA cleavage factor); or (lane 4) HeLa cells, 18 hours after infection, in the presence of Ara-C (an inhibitor of viral DNA replication and therefore late viral gene expression also); or (lane 7), purified vaccinia virus particles. Purification of the factor is described in Example 6, as are characterizing data.

One skilled in the art will appreciate that the identification of the AX element and above-described factor makes possible the generation of sequence-specific cleavage in RNAs other than those encoding the ATI protein. As will be clear from the Examples that follow, the factor effecting the site-specific cleavage is either induced or activated during the course of viral replication and may in fact be encoded by the virus. In any case, use of that factor, together with the AX element, makes it possible to effect site-specific cleavage, either in vivo or in vitro, of an RNA containing the AX element (or functional equivalent). Such directed cleavage can be used to abrogate the function of the target RNA or alter its properties, including stability, efficiency of translation, ability to be processed, ability to interact with other cellular nucleic acids or proteins, and ability to function as an enzyme or component thereof. One skilled in the art will appreciate that the AX element can be used with the factor for purposes similar to those for which restriction enzymes and their corresponding restriction sites are used (eg, for bioengineering specific RNA molecules).

Further, the artisan will appreciate that it should be possible to induce uninfected or infected cells (cells that do not encode the factor might be engineered to do so) to synthesize the factor thereby allowing the factor to cleave specific RNAs containing a cleavable element. It may be possible to alter the specificity of the factor, directing it to cleave novel targets such as essential RNAs of pathogenic agents (eg viruses) or endogenous RNAs involved in diseases (eg mRNAs encoding proteins that contribute to carcinogenesis, or mRNAs cytokines that induce processes that may be harmful in certain instances such as cytokine-mediated processes contributing to inflammatory diseases, or in mRNAs encoding autoimmune antibodies etc.). In this way a cell producing the modified factor would be able to prevent replication of an invading pathogen, or to be rendered incompetent to generate either specific proteins or nucleic acids that contribute to certain disease processes.

The non-limiting Examples that follow additionally define certain aspects of the invention.

EXAMPLES

The following protocols and experimental details are referenced in Examples 1 and 2 below. (See also Antczak et al, Proc. Natl. Acad. Sci., USA, 89:12033 (1992)).

Viruses and cells:

Vaccinia virus (Western Reserve strain), vaccinia virus vTF-3 (Fuerst, et al, Proc. Natl. Acad. Sci. USA, 83:8122 (1986)) and vaccinia virus recombinants were cultured either in human 143 cells or HeLa S3 cells, as described (Patel et al, EMBO J., 6:3787 (1987); Holowczak et al, Virology, 33:717 (1967)).

Construction of vaccinia virus A461:

An 850 base pair (bp) BamHI fragment containing the coding region for the bacterial chloramphenicol acetyltransferase (CAT) gene was isolated from plasmid p863 (obtained from E. Linney, Duke University, Durham, NC), which is a derivative of pSV2-cat$^S$ (Gorman et al, Mol. Cell Biol., 2:104 (1982)). This was inserted into the BamHI site in pTF7-5 (Fuerst et al, Mol. Cell Biol., 7:2538 (1987)), generating plasmid p1373, in which the CAT gene was in the same orientation as the phage T7 promoter. A 2080 bp EcoRI fragment containing the region corresponding to the 3' end of the late mRNAs encoding the major ATI protein was obtained from the KpnI G-fragment of the DNA of cowpox virus (Patel et al, EMBO J., 6:3787 (1987)). This fragment was inserted at the EcoRI site in the CAT gene in p1373, generating plasmid p2098, in which the viral thymidine kinase gene, the phage T7 promoter, the CAT gene, and the 3' end of the gene encoding the ATI protein, were all in the same orientation. A vaccinia virus recombinant, A461, containing this gene construction (see FIG. 1) was generated by standard procedures (Mackett et al, J. Virol., 49:857 (1984)), using plasmid p2098 as the insertion vector.

Preparation of whole-cell extracts:

Whole-cell extracts were prepared as described (Manley et al, Methods Enzymol., 101:568 (1983)) from uninfected HeLa cells; HeLa cells infected with vaccinia virus; and mouse L cells infected with vaccinia virus. Cells were infected with 10 plaque-forming units of virus per cell. The protein concentration of each extract was adjusted to 3.25 mg/ml.

RNA cleavage assays:

Unlabeled and $^{32}$P-labeled RNA substrates were prepared by in vitro transcription (Parsons et al, Virology, 175:69 (1990)) of the DNA of plasmid p2098 after it had been linearized with NcoI. This generated 2.7 kilobase (kb) RNAs containing the interrupted CAT gene. Cleavage of these RNAs was assayed at 30° C. in 25 µl reaction mixtures containing 40 mM Tris-HCl, pH 7.9; 40 mM KCl; 6 mM NaCl; 7.6 mM MgCl$_2$; 0.08 mM EDTA; 0.8 mM dithiothreitol; 1.2 mM ATP; 0.12 mM spermidine; 6% (vol/vol) glycerol; 8–10 µg protein (from 2.5 µl of whole-cell extract); and 1.5 µg substrate RNA. RNAs were recovered by ethanol precipitation after proteins had been removed by phenol/chloroform extraction. Before RNA analyses, DNA was removed by RNase-free DNase I. The $^{32}$P-labeled RNAs were resolved by electrophoresis in 1.6% agarose gels containing 2.2M formaldehyde, and visualized by autoradiography of the dried gels. Reovirus single-stranded RNAs used as size standards were synthesized in vitro as described (Skehel et al, Virology, 96:368 (1979)).

RNA analyses:

Nuclease S1 protection analyses were used to characterize the structure of the 5' and 3' ends of cleaved RNAs. Reaction conditions were as described (Patel et al, EMBO J., 6:3787 (1987)) except that nuclease S1 was used at a concentration of 1000 units/ml. Primer extension analysis (Patel et al, EMBO J., 6:3787 (1987); Krug et al, Methods Enzymol., 152:316 (1987)), were used to characterize the structures of RNA 5' ends.

EXAMPLE 1

Figure 1:
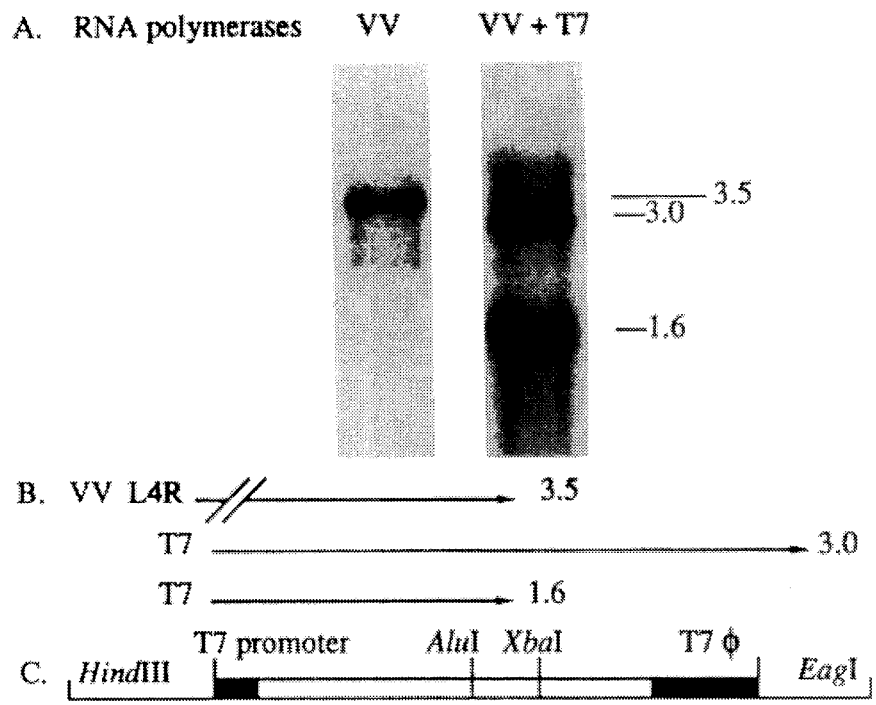
FIG. 1: Site-specific RNA 3' end formation is not dependent upon either the promoter or the RNA polymerase. (A) Northern blot analysis of late RNAs synthesized in cells infected with either vaccinia virus A461 (VV) or with A461 and vaccinia virus vTF73, which encodes the phage T7 RNA polymerase (VV+T7). RNAs were extracted from cells 20 hours after infection, resolved by electrophoresis in a 1% agarose gel containing 2.2M formaldehyde, and then transferred to a nylon membrane. Transcripts of the CAT gene were detected by DNA-RNA hybridization using a probe specific for CAT gene sequences. The sizes of the CAT transcripts are indicated in kilobases (kb). (B) Map of the various CAT transcription units. Transcription is under the control of either the late promoter of the vaccinia virus L4R gene or the phage T7 promoter (RNA lengths are indicated in kb). Arrowheads indicate the positions of the RNA 3' ends. (C) Composition of the portion of the vaccinia virus HindIIIJ fragment containing the modified CAT gene inserted into the viral thymidine kinase gene. This construction is contained both in plasmid p2098 and in virus A461. It comprises the phage T7 promoter and transcription termination signal (φ) flanking the CAT gene (black bars) interrupted by the 2080 bp EcoRI fragment of the KpnIG fragment of cowpox virus DNA (open bar). The AluI-XbaI fragment containing the AX element is within this fragment.

RNA 3' End Formation is Not Dependent Upon Either the Promoter or the RNA Polymerase A cis-acting element directing the site-specific formation of 3' end of the mRNAs encoding the ATI protein has been identified within the 347 -bp AluI-XbaI fragment containing the sequence corresponding to the 3' end of the mRNA. When a DNA fragment containing this element (designated the AX element) was placed downstream of a CAT gene under the control of a T7 RNA polymerase promoter (within the thymidine kinase gene) in the genome of vaccinia virus A461, it directed the formation of late RNAs of a defined length that suggested these RNAs were transcribed from the promoter of the L4R gene (FIG. 1). This demonstrated both that the AX element functions in vaccinia virus as well as cowpox virus, and that it functions downstream of late promoters other than that of the gene encoding the ATI protein. Moreover, when cells were co-infected with vaccinia virus vTF73, which synthesizes the T7 RNA polymerase, additional CAT transcripts were formed (FIG. 1). Allowing for the additional length caused by the polyadenylation of these RNAs, the 3' ends of these RNAs correspond either to the position of the T7 transcriptional terminator or to the position of the AX element. In contrast, in vitro transcription of the identical DNA template with T7 RNA polymerase failed to generate any CAT transcripts with defined 3' ends other than those corresponding to the site of the T7 transcriptional terminator. This indicated that the AX element did not act as a transcriptional termination signal for the T7 RNA polymerase. Significantly, these results demonstrated that the AX element could direct RNA 3' end formation efficiently in cells whether the RNA was generated by the multisubunit RNA polymerase of the poxvirus or the single polypeptide RNA polymerase of phage T7.

EXAMPLE 2

3' Ends are Generated by Site-Specific RNA Cleavage

The lack of dependence upon either promoter or RNA polymerase suggested that the site-specific 3' end formation occurs by a post-transcriptional mechanism. To test this hypothesis, in vitro synthesized RNAs containing the AX element were added to extracts of uninfected or virus-infected cells to assay for 3' end formation dependent upon the AX element. The $^{32}$P-labeled RNA substrate used in these assays was a 2.7-kb in vitro transcription product of the T7 promoter-CAT gene construct present in plasmid p2098. This in vitro synthesized RNA was equivalent to the 3.0 kb RNA generated by T7 RNA polymerase in the cells (FIG. 1). When the 2.7-kb RNA substrate was incubated in the presence of an extract of HeLa cells infected with vaccinia virus it was converted into two fragments, one about 1.1 kb long and the other about 1.6 kb long (FIG. 2). Similar conversion was not detected when the RNA was incubated either in buffer alone, or in extracts from uninfected cells, suggesting that the conversion required a virus-induced factor. Moreover, the sizes of the fragments generated in the extracts of the virus-infected cells suggested that these RNAs were generated by endoribonucleolytic cleavage of the 2.7 kb RNA at a position within the AX element in the RNA. An RNA cleavage at this site would generate the 3' end of a 1.6-kb RNA and the 5' end of a 1.1-kb RNA.

Figure 3:
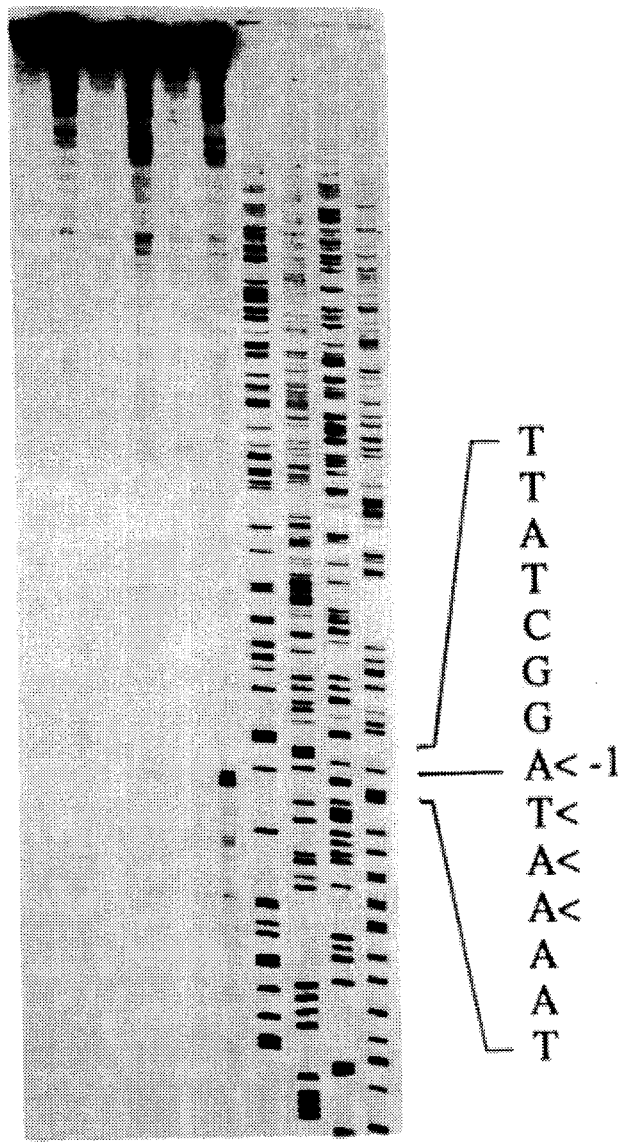
FIG. 3: Nuclease S1 protection analysis of the 3' ends of RNAs generated by cleavage in vitro. Unlabeled 2.7 kb RNAs (p2098-derived) were incubated for 60 minutes either in extracts of uninfected HeLa cells, or in extracts of HeLa cells prepared 15 hours after they had been infected with vaccinia virus. After extraction from the reaction mixtures these RNAs, and also untreated 2.7 kb RNAs, and yeast tRNAs, were separately annealed to a $^{32}$P-labeled probe DNA consisting of a 1650 bp HinPI-BamHI fragment (3' end-labeled at HinPI site) containing the sequence corresponding to the position of the RNA 3' end-site. Residual single-stranded nucleic acids were digested with nuclease S1. Nuclease-resistant products were resolved by electrophoresis in a 5% polyacrylamide gel containing 8.3M urea. The $^{32}$P-labeled DNA was visualized by autoradiography. Lanes 1–6 contain portions of the DNA probe protected by hybridization to yeast tRNAs (lane 1); untreated 2.7 kb RNAs after incubation in the extract of uninfected cells (lane 4); endogenous RNAs present in the extract of virus-infected cells (lane 5); and the 2.7 kb RNAs after incubation in the extract of virus-infected cells (lane 6). Lanes 7–10 contained the products of chain-termination sequence reaction using M13mp18 single-stranded DNA as the template, co-electrophoresed to provide size markers. The probe DNA sequence containing the nucleotide (designated-1) complementary to that at the 3' end of the RNA is indicated. Arrows indicate the major end-points of complementarity between the probe and the cleaved RNAs (SEQ ID NO:11).

Nuclease S1 protection analyses confirmed the generation of RNA 3' ends corresponding to a site within the AX element (FIG. 3). End-points of complementarity between the probe and the RNA, which corresponded to a region in the AX element about 130 nucleotides downstream of the AluI recognition sequence, were readily detectable after the 2.7-kb RNAs had been incubated in the presence of an extract of virus-infected cells (FIG. 3, lane 6). However, similar end-points of complementarity were not detected if the RNA substrate had been incubated in extracts of uninfected cells (FIG. 3, lanes 4). This result indicated that a factor in the virus-infected cells generated the formation of a novel RNA 3'-end whose sequence was 5'AUUUUAU3'. The position of this end-point was consistent both with the predicted site of the 3' end of the 1.6-kb RNAs, and the nucleotide sequence at the 3' end of mRNAs encoding the ATI protein (see Example 3).

Figure 4:
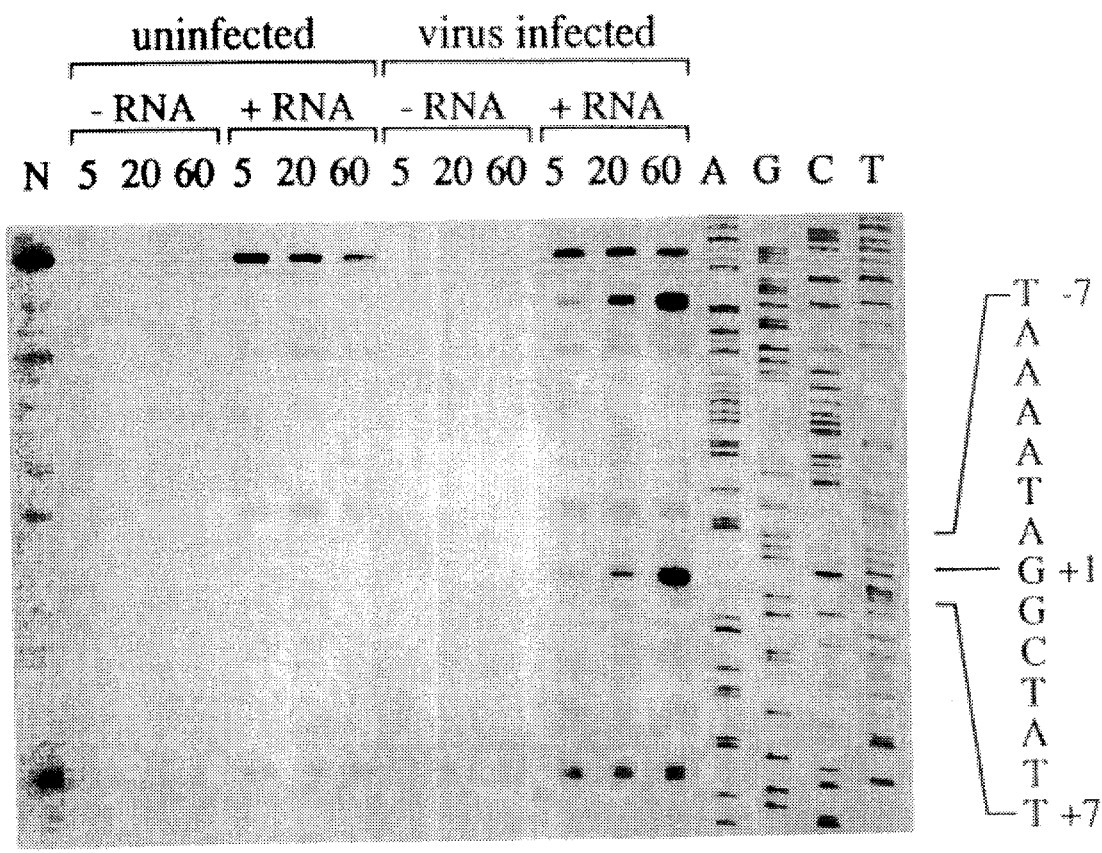
FIG. 4: Primer extension analysis of the 5' ends of RNA products generated by cleavage in vitro. Unlabeled 2.7 kb RNAs (p2098-derived) were incubated for 5, 20, or 60 minutes either in extracts of uninfected HeLa cells, or in extracts of HeLa cells prepared 15 hours after they had been infected with vaccinia virus. Oligonucleotides (5'CGG-GATCCGTAACGAAACATCCATCG-3') (SEQ ID NO:1), labeled at their 5' ends with $^{32}$P, were annealed to RNAs recovered either from these reactions mixtures (+RNA) or from unsupplemented extracts (–RNA). After DNA synthesis, the cDNA products were resolved by electrophoresis in a 6% polyacrylamide gel containing 8.3M urea, and were visualized by autoradiography. Lane N, products of DNA synthesis using untreated 2.7-kb RNAs as substrate; lanes A, G, C, and T, products of sequence reactions that were co-electrophoresed to provide size markers. The predicted sequence of the cDNA containing the nucleotide (designated +1) at the first major end-point of cDNA synthesis is indicated (SEQ ID NO:12).
Figure 5:
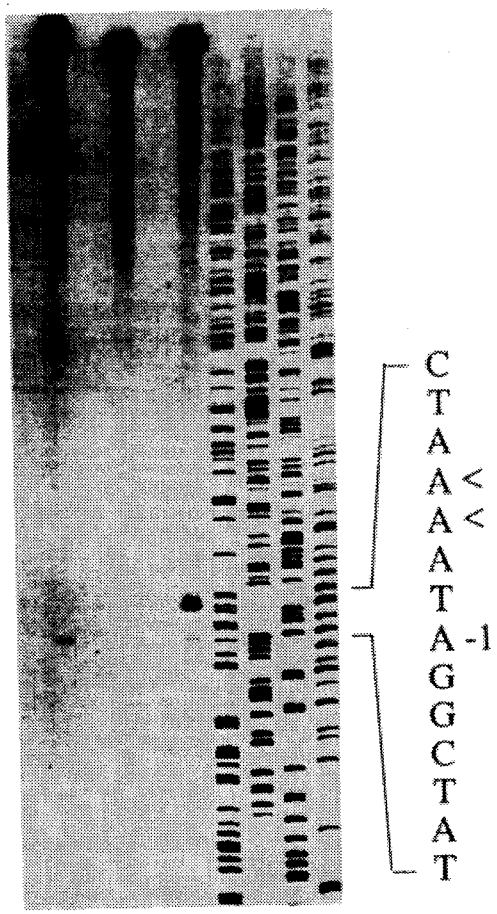
FIG. 5: Nuclease S1 protection analysis of the 5' ends of RNAs generated by cleavage in vitro. Unlabeled 2.7-kb RNAs (p2098-derived) were incubated for 60 minutes either in extracts of uninfected HeLa cells or in extracts of HeLa cells prepared 15 hours after they had been infected with vaccinia virus. After extraction from the reaction mixtures these RNAs, and yeast tRNAs, were separately annealed to $^{32}$P-labeled probe DNA consisting of a 1455 bp EcoRI-XbaI fragment (5' end-labeled at XbaI site) containing the sequence corresponding to the position of the RNA 5' end-site. Residual single-stranded nucleic acids were digested with nuclease S1. Nuclease-resistant products were resolved by electrophoresis in a 6% polyacrylamide gel containing 8.3M urea. The $^{32}$P-labeled DNA was visualized by autoradiography. Lanes 1–6 contained portions of the DNA probe protected by hybridization to yeast tRNAs (lane 1); untreated 2.7-kb RNAs (lane 2); endogenous RNAs present in the extract of uninfected cells (lane 3); the 2.7 kb RNAs after incubation in the extract of uninfected cells (lane 4); endogenous RNAs present in the extract of virus-infected cells (lane 5); and the 2.7-kb RNAs after incubation in the extract of virus-infected cells (lane 6). Lanes 7–10 contained the products of sequence reactions using M13mp18 single-stranded DNA as the template, which were co-electrophoresed to provide size markers. The sequence of the part of the DNA probe containing the nucleotide (designated-1) complementary to that at the 3' end of the RNA is indicated. Arrows indicate the major endpoints of complementarity between the probe and the cleaved RNAs (SEQ ID NO:13).

The generation of 5' ends corresponding to the sequence downstream of the predicted cleavage site within the AX element was detected by primer extension and nuclease S1 protection analyses. Extension of a primer, which annealed to the RNA substrate about 70 nucleotides downstream of the predicted RNA cleavage site, generated two cDNA products that were only produced if the RNA substrate had been incubated in the presence of extract of virus-infected cells (FIG. 4). The shorter of these two cDNA products was 98 nucleotides long, suggesting that it was derived from an RNA whose 5' end mapped to the predicted site of RNA cleavage. In the RNA substrate, this sequence, 5'CCGAUAA3', is immediately downstream of the sequence present at the 3' ends of the 1.6 kb RNAs. The length of the other major cDNA product, about 168 nucleotides, indicated a cDNA 3' end that did not correspond to either the position of any identified RNA 3' ends. This suggested that the longer cDNAs may have been the products of second-strand cDNA synthesis. Consistent with this interpretation, nuclease S1 protection analysis (FIG. 5) identified only a single endpoint of complementarity between the 5' ends of the RNA products and a probe extending 1.3 kb upstream of the position of the predicted RNA cleavage site. This single endpoint of complementarity corresponded closely to the position of the sequence 5'CCGAUAA3', which the primer extension analysis (FIG. 4) had predicted to be at the 5' end of the RNA.

Figure 6:
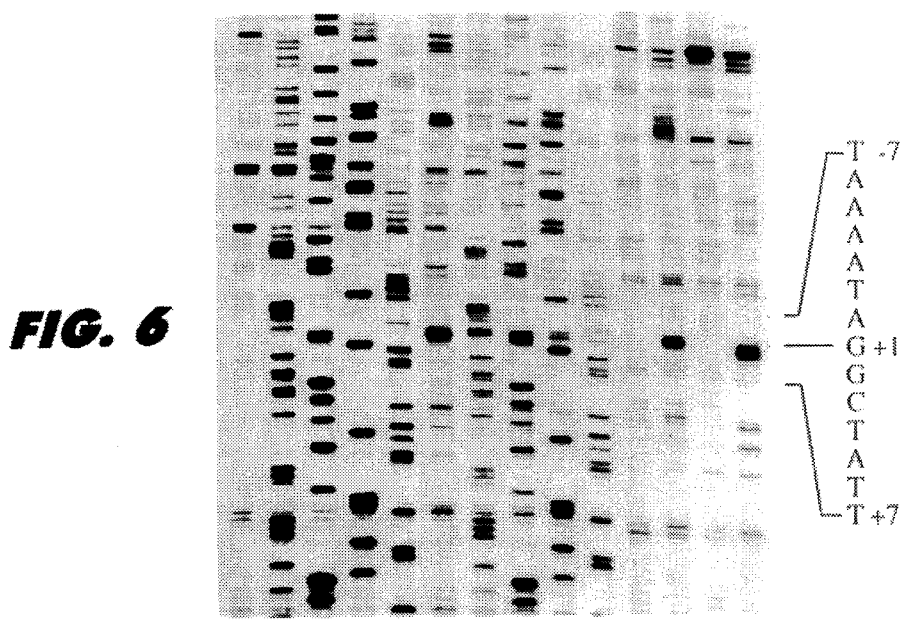
FIG. 6: Nucleotide sequence analysis of the 5' ends of RNAs generated by in vitro cleavage. Conditions for primer extension analysis of either untreated 2.7-kb substrate RNAs, or substrate RNAs that had been incubated in extracts prepared from cells 15 hours after they had been infected with vaccinia virus were as described in FIG. 4, except that reactions were performed either in the absence of dideoxynucleotides (0), or in the presence of 10 μM dideoxy–ATP, –GTP, –CTP, or –TTP (lanes A, G, C and T). Primer extensions were also performed in the absence (–PPi) or presence (+PPi) of 4 mM sodium pyrophosphate, using the same RNA samples, designated U (untreated RNAs) or V (RNAs incubated in extracts of virus-infected cells). The concentration of each of the four dNTPs in these reactions was 500 μM. Products were resolved by electrophoresis in a 6% polyacrylamide gel containing 8.3M urea and visualized by autoradiography. The cDNA sequence containing the nucleotide (designed +1) at the first major end-point cDNA synthesis is indicated. The longer cDNAs are derived from the uncleaved RNA substrate (SEQ ID NO:14).

Primer extension in the presence of dideooxynucleotides generated chain-terminated products corresponding to the sequence of the partially cleaved RNA template (FIG. 6). This confirmed that the primer had annealed at a single position in the substrate RNA. The sequence analysis directly demonstrated that the sequence at the 5' ends of the RNAs that were generated by incubation of the RNA substrate in extracts of virus-infected cells was 5'CCGAUAA3'. Furthermore, under these reaction conditions, and in the presence of 4 mM sodium pyrophosphate, which inhibits both second-strand cDNA synthesis and the premature termination of reverse transcription (Krug et al, Methods Enzymol, 152:316 (1987)), significant quantities of the 168 nucleotide cDNAs were not generated.

The identification of novel 3' and 5' RNA ends corresponding to adjacent nucleotides in the substrate RNA within the AX element (FIG. 7) confirmed that a single endonucleolytic event generated the two RNA products. The identification of these cleavage products only after incubation of the substrate RNA in the presence of extract of cells prepared during the late stages of viral replication indicates that the factor responsible for the RNA cleavage is either virus-induced or virus-encoded. Site-specific RNA cleavage was not observed in extracts prepared during the early stage of virus replication. When the RNA substrate was incubated in these extracts, it was rapidly degraded.

EXAMPLE 3

Identification of the Sequence at the 3' End of the Late mRNA Encoding the 160 kDa ATI Protein S1 nuclease protection analysis was used to identify the end-point of complementarity between the 3' end of the RNAs and the DNA template strand. The results (FIG. 8) confirmed the homogenous nature of the 3' ends that had been suggested by previous RNA hybridization analyses (Patel and Pickup, EMBO J. 6:3787 (1987)). There was no indication from this analysis that any significant proportion of the RNAs had 3' ends corresponding to positions within about 200 bp of the identified end-point. In addition, it indicated that the 3' ends of the RNA corresponded to a region about 150 nucleotides downstream of the Alu I site indicated in FIGS. 9 and 10.

Although the S1 nuclease protection analysis provided a good indication of the nature of the end-points of complementarity between the majority of the RNAs and the DNA, analyses of this type cannot resolve end-points to within a single base, nor can they provide any information on the presence or nature of any downstream sequences that are not complementary to the DNA. The presence of a 3' poly(A) tail was expected but, because of the presence of 5' poly(A) sequences in these RNAs (Patel and Pickup, EMBO J. 6:3783 (1987)), the ability of these RNAs to hybridize with oligo dT cellulose did not demonstrate this. Therefore, to gain more precise information on the nature of the 3' ends of these RNAs, cDNA derived from the 3' ends of RNAs of both the cowpox virus 160K gene and the vaccinia virus 94K gene were generated, and their nucleotide sequences were determined.

The cDNAs were generated according to the RACE procedure (Frohman et al, Proc. Natl. Acad. Sci. USA 85:8998 (1988), Kawasaki et al, Proc. Natl. Acad. Sci. USA 85:5698 (1988)) in which the synthesis of the first strand of the cDNA was by extension of an oligo dT containing primer designed to anneal with the poly(A) present in a 3' poly(A) tail. The success of this procedure demonstrated that 160K gene RNAs possessed 3' poly(A) tails. The cDNAs derived from the 3' ends of 160K gene mRNAs were amplified by PCR. Reverse transcription was performed using a 33-base single-stranded DNA primer designated "160KdT" which consisted of the sequence 5'-GCCTGCAGGCGGC-CGCTTTTTTTTTTTTTTTTTT-3'(SEQ ID NO:2). This primer was designed to promote reverse transcription of RNA molecules polyadenylated at their 3' termini via the 17 T's located at the 3' end of the primer; in addition, it possessed a 5' "adapter" sequence containing Pst I and Not I restriction sites used for cloning the PCR-amplified cDNA.

Figures 7, 8:
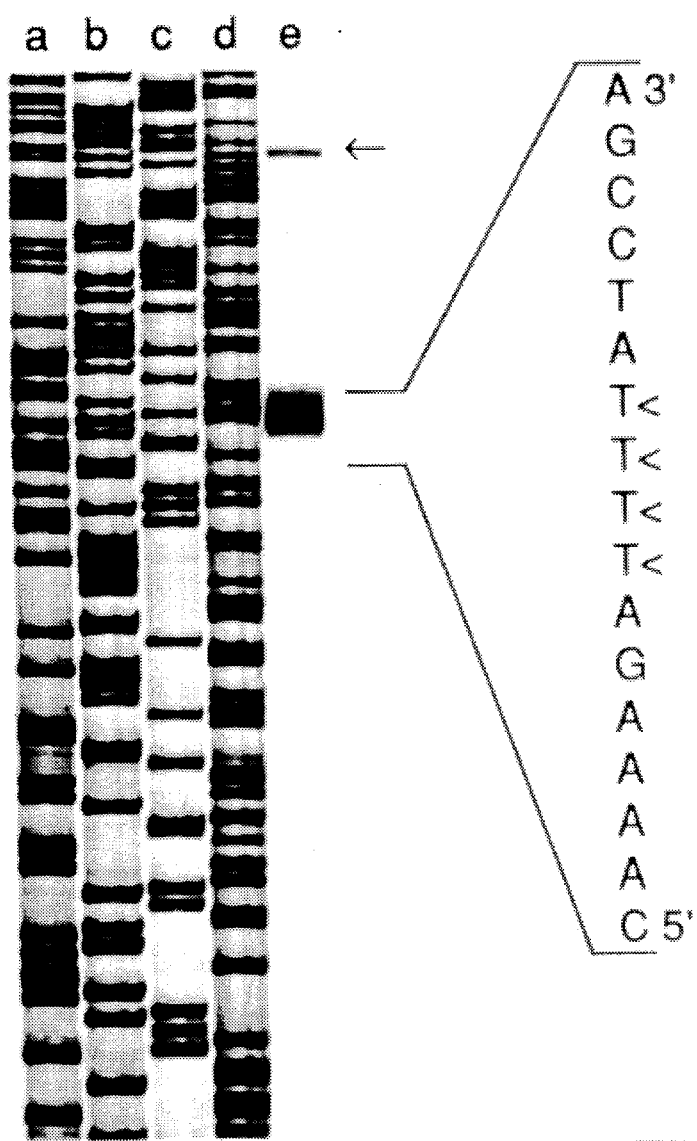
FIG. 7: The cleavage site in the AX element. The cleavage site in the primary RNA is indicated by the arrow. The 3' polyadenylated form of the mature RNA is shown beneath the sequence of the primary RNA (SEQ NO ID:15 and SEQ ID NO:16).
FIG. 8: Nuclease S1 protection analysis of the extent of complementarity between the 3'-ends of 160K mRNAs and the cowpox (CPV) virus genome. A 307 bp Hin PI-ClaI fragment, which overlaps the first 227 nucleotides of the sequence shown in FIG. 10, was 3'-end labeled at the Hin PI site, and hybridized with RNA extracted from CPV-infected cells. Residual single-stranded nucleic acids were digested with nuclease S1. The nuclease S1-resistant products were resolved by electrophoresis in an 8% polyacrylamide/7M urea gel. The labeled nucleic acids were visualized by autoradiography of the dried gel. The products of dideoxynucleotide chain-termination reactions (lanes a, b, c and d) were co-electrophoresed to provide size markers. The nuclease S1-resistant material is shown in lane e. The sequence of the coding strand, with respect to the 160K gene, is shown. The arrowheads indicate the 5'-ends of the protected DNAs. The DNA indicated by the arrow is full-length protected probe (SEQ NO ID:17).

Specific amplification of cDNA derived from the 3' termini of CPV 160K gene transcripts was obtained using a polymerase chain reaction procedure (Kawasaki In: PCR Protocols: A Guide to Methods and Applications, Eds. M.A. Iunis et al, Chapter 3 pp. 21–27 (1990)) employing two unique single-stranded DNA primers. The first primer, designated "160KPS", consisted of the 28-base sequence 5'-GCTCTAGAGAGTTAAATGCCTCAGACGC-3'(SEQ ID NO:3), which contained a 5' XbaI restriction site (for cloning) and a 20-base 3' sequence (underlined here and in FIG. 10) that is identical to a sequence located in the CPV genome approximately 405 bp downstream of the end of the 160K protein coding region. Since it was the same sense as 160K mRNA, the primer would be complementary to cDNA derived by reverse transcription of 160K gene transcripts that extended more than 425 bp downstream from the 3' end of the 160K protein coding sequence, and was designed to specifically prime second-strand synthesis from such cDNA molecules. The second primer, designated "160K3PR", was a 13-mer with the sequence 5'-GCCTGCAGGCGGC-3'(SEQ ID NO:4). This primer was identical in sequence to the first 13 nt at the 5' end of the reverse transcription primer, 160KdT, and was used to prime synthesis of strands during PCR amplification that were complementary to full-length strands derived by second-strand synthesis. Thus, full-length, PCR-amplified duplex DNA derived in this way would possess an Xba I site at one end, and Pst I and Not I sites at the opposite end.

The majority of the PCR products were about 130–250 base pairs long, consistent with the length between the position of the sequence complementary to the 160KPS primer and the end-point of complementarity between the RNA and the DNA (FIG. 8), plus some base pairs from the 3' poly(A) tail. The amplified cDNAs were fractionated by gel electrophoresis (8 fractions containing DNAs from 150–600 bp long). The DNAs in each fraction were separately ligated into the plasmid vector pGEM3Z, and the products of the ligations were used to transform *E. coli* JM109 cells. Plasmid DNAs from 36 transformants selected at random from each of the eight groups of transformants were analyzed by restriction enzyme cleavage with PstI and XbaI. Inserts were detected that ranged in size from approximately 145 to 210 bp, consistent with the lengths of the major products of the PCR amplification. However, plasmids with inserts similar in length to some of the longer (between 210 and 600 base pairs) but less abundant products of the PCR amplification were not recovered.

The nucleotide sequences of 20 of these cloned cDNAs, including all cDNAs that could be differentiated by their electrophoretic mobility, were determined. The results of this analysis are summarized in Table 1.

TABLE 1

| Nucleotide sequences at the 3' ends of cDNAs | |
|---|---|
| Sequence at the 3' end of the cDNA | No. of isolates |
| Cowpox virus 160K gene RNAs | |
| (−15) CACAAAAGAUUUUAUA$_{(17)}$* (SEQ ID NO: 5) | 1 |
| (−15) CACAAAAGAUUUUAUA$_{(18)}$ (SEQ ID NO: 35) | 2 |
| (−15) CACAAAAGAUUUUAUA$_{(18)}$ | 2 |
| (−15) CACAAAAGAUUUUAUA$_{(19)}$ (SEQ ID NO: 36) **−69 A to G | 2 |
| (−15) CACAAAAGAUUUUAUA$_{(20)}$ (SEQ ID NO: 37) | 1 |
| (−15) CACAAAAGAUUUUAUA$_{(22)}$ (SEQ ID NO: 38) ** −60 U to C | 2 |
| (−15) CACAAAAGAUUUUAUA$_{(26)}$ | 1 |
| (−15) CACAAAAGAUUUUAUA$_{(29)}$ (SEQ ID NO: 40) | 3 |
| (−15) CACAAAAGAUUUUAUA$_{(40)}$ (SEQ ID NO: 41) | 1 |
| (−15) CACAAAAGAUUUUAU$\underline{AUUA}_{(18)}$ (SEQ ID NO: 6) | 2 |
| (−15) CAAAA$\underline{C}$A$_{(19)}$ (SEQ ID NO: 42) | 1 |
| (−15) CACAAAAGAUUUUAUC..UUGUUA$_{(31)}$ (+51) (SEQ ID NO: 7) | 1 |
| Vaccinia virus 94K gene RNAs | |
| (−15) CACAAAAGAUUUUAUA$_{(17)}$ | 1 |
| (−15) CACAAAAGAUUUUAUA$_{(18)}$ | 1 |
| (−15) CACAAAAGAUUUUAUA$_{(21)}$ (SEQ ID NO: 43) **−16 U to C | 1 |
| (-35) CA$_{(36)}$ (SEQ ID NO: 44) | 1 |

*number of adenylates
and underlined nucleotides indicate base change from sequence in the viral DNA The majority of these cDNAs contained the 108 bp sequence corresponding to the region between the sequence complementary to the 160KPS primer and the sequence 5'-UUUUAU-3' at the end-point of complementarity between the RNA and the DNA template strand (FIG. 10**). Therefore, the last uridylate residue in the RNA, and its corresponding adenylate in the template strand of the DNA, were designated −1 relative to the position of the major 3' end of the mRNA. Downstream of the −1 nucleotide, each of these cDNAs had a run of adenylates (17 to 40) corresponding to the 3' poly A tails of the RNAs. The difference between the lengths of the cloned inserts and the lengths of the PCR generated fragments may reflect an instability of long poly(A) stretches in the bacterial plasmids, as evidenced by the failure to recover any cloned eDNA containing a poly(A) sequence of more than 40 residues. Previous analyses indicated that the 160K mRNAs were about 4.5 kilobases long (Patel and Pickup EMBO J. 6:3787 (1987)). Therefore, taking into account the 5' poly(A) sequences of about 20 nucleotides, and also the specific 3' end of these mRNAs, this suggests that the majority of these mRNAs each contain about 100 adenylates at their 3' end. Four of the other characterized cDNAs were derived from the 3' ends of 160K mRNA, but each of these differed from the other cDNAs. Two of these cDNAs contained the sequence ATT at +1 to +3. This sequence was apparently derived in a template-independent manner, presumably during reverse transcription or PCR amplification, because the corresponding sequence was in the DNA template strand is 5'-CCG-3'. One cDNA was apparently derived from a 160K mRNA the 3' end of which was 50 nucleotides downstream of the usual 3' end site. Similarly, a fourth cDNA was obtained, the sequence of which suggested a 3' end at −14 followed by the sequence $A_{(3)}CA_{(19)}$. Presumably, the C may also have been added in a template-independent manner, perhaps misincorporated for an A during the cloning procedure. The predicted 3' ends at +50 and −14 represent either an artefact of the cloning procedure or uncommon 160K gene RNAs, because RNAs whose 3' ends corresponded to either of these positions were not detected by S1 nuclease protection analyses (FIG. 8). One cDNA was obtained that was not derived from the 160K gene; its origin is unknown.

Analysis of the 3' ends of cDNAs of the vaccinia virus mRNAs encoding the 94 kDa equivalent of the CPV 160 kDa protein revealed similar 3' end structures (Table 1) consistent with the identical nature of the sequences of the DNAs of viruses of these two types in the region containing the signal directing the RNA 3' end formation.

These data indicate that the majority of the mature mRNAs of the 160K gene have 3' ends (excluding the 3' poly A sequences) that correspond to the U residue (or the equivalent T residue in FIG. 10) designated −1 (the residue to the left of the vertical bar). This U reside (−1) is the 3' terminal residue generated by in vitro cleavage of the AX element in the 2.7 kb RNA as described in Example 2.

EXAMPLE 4

A Cis-Acting Element within the 347 bp Alu I-Xba I Fragment Directs RNA 3' End Formation To determine the identity of the cis-acting signal directing the sequence-specific RNA 3' end formation, portions of the 347 Alu-I-Xba I fragment containing the sequence corresponding to the end of the RNAs were tested for the ability to direct RNA 3' end formation. For this purpose, thirteen recombinant vaccinia viruses were generated, each containing the CAT gene under the control of the CPV160K gene promoter upstream of either the intact 347 Alu-I-Xba I fragment, or variants of this fragment, as described in FIGS. 9–11. Late RNAs were extracted from cells infected with these recombinant viruses. The CAT gene RNAs produced by these viruses were analyzed by hybridization as shown in FIG. 12. The results demonstrated that the Alu I-Xba I fragment contains the information necessary to direct the formation of sequence specific 3' ends (lane a). Moreover, sequence analysis of cDNA copies of the 3' ends of these CAT transcripts showed that the ends of the transcripts were identical to those of the authentic mRNAs encoding the ATI protein (data not shown). Reversal of the orientation of the Alu I-Xba I fragment abrogated its ability to direct 3' end formation (lane m). Tandem duplication of the cis-acting element as shown in FIG. 9 (G) resulted in the formation of ends corresponding only to the upstream element (FIG. 12, lane b), confirming that 3' end formation is not simply a function of this element activating to stabilize the RNAs against degradation from 3' exonucleases.

To better define the sequence element directing 3' end formation, a series of deletion variants of the Alu I-Xba I fragment were examined for their ability to direct 3' end formation (FIGS. 10–12). Deletion of sequences to within 15 base pairs upstream of the 3' end site did not affect 3' end formation, but deletion of sequences to one base pair upstream of the 3' end site removed sequence information necessary to effect 3' end formation (FIGS. 11 and 12, lanes b–e). Analysis of the effects of 3' deletions of the Alu I-Xba I fragment showed that the removal of sequences to within 38 base pairs downstream of the 3' end site did not affect 3' end formation, but deletion to base pair 20 abrogated 3' end formation (FIGS. 11 and 12, lanes e–k). Therefore, most of the element required for 3' end formation is downstream of the 3' end site. Moreover, these analyses provided further evidence that the element is not merely providing a region that protects the RNA from 3' exonuclease degradation, because most of this element is not present in the stable, mature mRNA.

EXAMPLE 5

Detailed Characterization of the AX Element (i) Additional 5' and 3' deletion analyses:

To map the boundaries of the AX element more precisely, additional 5' and 3' deletion mutants of the AX element were constructed and inserted into the genome of vaccinia virus as described in Example 4 for the other deletion mutations. FIG. 13 (A and B) show the extent of the various 5' deletions (to −10 and −5) and 3' deletions (to +35, +30, and +25) of the sequence present in the wild-type RNA containing a functional AX element.

Northern blot analyses of late CAT RNAs containing these mutated AX elements showed that 5' deletions to either −10 or −5 did not prevent cleavage of the AX element. These analyses also showed that deletion to +25 or to +30, but not to +35, could drastically reduce or eliminate cleavage of the AX element.

(ii) Linker-scanning mutation analysis of the AX element:

A series of linker scanning mutations consisting of 5-nucleotide substitutions of the region +1 to +30 (FIG. 13, C) of the AX element were placed downstream of the CAT gene under the control of the CPV160K gene promoter in the genome of vaccinia virus as described above for the deletion mutation analysis. Northern blot analyses of late CAT RNAs containing these mutated AX elements showed that substitution of the sequences between +1 and +5 and the sequences between +26 and +30 either eliminated or drastically reduced the cleavage of the mutated AX element in cells. In contrast, substitution of sequences between +6 and +25 had little or no effect on the efficiency with which the AX element was cleaved in cells. These data derived from the linker scanning mutations are consistent with those data derived from the 5' and 3' deletion analyses.

EXAMPLE 6

Characterization of Factor from Extracts of Vaccinia-Virus-Infected Cells

HeLa cells ($10 \times 10^9$) infected with vaccinia virus (5–10 pfu/cell) were harvested at late times in virus infection (12–20 h). (All subsequent purification procedures were performed at approximately 5° C.). The cells were allowed to swell in 125 ml of buffer A (25 mM Tris-HCl, pH 8.0 at 25 C; 1 mM $MgCl_2$; 0.1 mM EDTA; 0.1 mM EGTA; 2 mM dithiothreitol) containing 10 mM NaCl. The swollen cells were disrupted using a Dounce homogenizer, a procedure that leaves the cell nuclei intact. Nuclei were separated from the cytoplasmic fraction by low speed centrifugation. The supernatant was decanted and saved. The pellet of nuclei was resuspended in 75 ml of 10 mM NaCl-buffer A, and the suspension was subjected to low speed centrifugation. The supernatant was decanted and pooled with the cytoplasmic fraction. The pool of supernatants (approximately 200 ml) was adjusted to 100 mM $MgCl_2$, incubated at 5° C. for 1 hour, and then subjected to centrifugation at approximately 100,000×g for 2.5 h. The supernatant (approximately 2.20 ml) was collected and adjusted to 15% saturation with solid ammonium sulfate. The precipitate that formed at this step was removed by centrifugation at approximately 10,000×g for 30 min. The supernatant was then adjusted to 45% saturation with ammonium sulfate. The precipitate that forms at this step was recovered as described above. Most of the cleavage activity present in the cytoplasmic fraction was recovered in the 25–45% ammonium sulphate precipitate. The precipitate, containing approximately 600 mg of protein, was resuspended in 10–15 ml of buffer A containing 50 mM NaCl and 15% (v/v) glycerol, and dialyzed extensively against the same buffer. The activity associated with the factor prepared in this manner was stable for at least 8 months when stored at −80° C.

The virus-induced, site-specific factor present in the 25–45% ammonium sulfate fraction just described was resolved by chromatography on a 2.5×5 cm column of heparin-Sepharose (Pharmacia LKB). The 25–45% ammonium sulfate fraction (approximately 300 mg) was applied in buffer A containing 50 mM NaCl and 15% glycerol. The column was developed by successive washes with buffer A (containing 10% glycerol) and increasing concentrations of NaCl, in increments of 200 mM between 200 and 1200 mM NaCl. Under these conditions, the factor eluted between 600 and 800 mM NaCl. The factor obtained in this manner was then applied to 10–40% (v/v) gradients of glycerol containing buffer A and 200 mM NaCl and was subjected to centrifugation at 275,000×g for 15 h. The location of the factor in the gradient was determined by assaying fractions of the glycerol gradient in the in vitro cleavage assay described by Antczak et al (Proc. Natl. Acad. Sci. USA 89:12033 (1992)). Protein molecular weight markers sedimented under identical conditions. The markers used were thyroglobulin (molecular weight 670,000), apoferritin (molecular weight 450,000), beta-amylase (molecular weight 200,000), alcohol dehydrogenase (molecular weight 150,000), albumin (molecular weight 66,000), and carbonic anhydrase (molecular weight 31,000). The factor sediments in this gradient at a position between that of albumin (molecular weight 66,000) and alcohol dehydrogenase (molecular weight 150,000).

Other chromatographic properties:

a) When the material present in the 25–45% ammonium sulfate fraction was applied to poly I:C-Sepharose (Pharmacia LKB) in buffer A at 50 mM NaCl, the factor bound at 50 mM NaCl and eluted at 200 mM NaCl.

b) Eight different reactive dyes crosslinked to agarose have also been tested for their ability to bind the factor from the 25–45% ammonium sulfate fraction. The factor remained bound to Blue 72-agarose (Sigma) at 400 mM NaCl, but was eluted at 1200 mM NaCl. The factor either eluted at lower salt concentrations from other dye columns with contaminating nonspecific ribonucleases, or else it did not elute from the columns even at NaCl concentrations as high as 1200 mM. Optimization of assay conditions using the dialyzed 25–45% ammonium sulfate fraction in buffer A at 200 mM NaCl:

a) The factor was most active at a NaCl concentration of about 200 mM, though activity was still be detected at 410 mM NaCl.

b) It was not necessary to supplement assays with nucleoside triphosphates, creatine phosphate, spermidine, or KCl in order to detect factor activity (see Antczak et al, Proc. Natl. Acad. Sci. USA 89:12033 (1992)).

c) The factor was active at 30° C. in a pH range from 5.2 to 7.7, and did not appear to be inactivated when stored in the same pH range at 5° C. for at least 24 h.

d) At a NaCl concentration of 10 mM, the factor precipitated at pH 6.0 and 6.5 (at 5° C.), but it could be recovered in an active form from the precipitate.

e) The factor was stable at 5° C. for at least 24 h when stored in buffers containing between 50 and 1200 mM NaCl.

f) The factor was inhibited by 10 mM EDTA concentrations (in excess of the magnesium concentration at 1 mM), but it was not inhibited by the same concentration of 10 mM EGTA.

g) The factor was inhibited by vanadyl ribonucleosides (10 mM) obtained from 5 Prime to 3 Prime, but was not inhibited by actinomycin D at 5 micrograms/ml or protein ribonuclease inhibitors such as RNasin (Promega) or Inhibit-ACE(5 Prime-3 Prime).

All documents mentioned hereinabove are hereby incorporated in their entirety by reference.

One skilled in the art will appreciate from a reading of the foregoing that various changes can be made in form and detail can be made without departing from the true scope of the invention.

What is claimed is:

1. An isolated RNA fragment having the sequence of SEQ ID NO:8 about 20 bases 5' to the sequence of SEQ ID NO:9.

2. A nucleic acid construct comprising a non-A-type inclusion protein-encoding sequence operably linked to a promoter and directly linked to a sequence that directs 3' end formation of an RNA transcript of said non-A-type inclusion protein-encoding sequence, wherein said 3' end formation directing sequence consists of a sequence:

i) defined by position 100 to position 347 of SEO ID NO:18 or ii) position 1 to position 223 of SEQ ID. NO:18, or portions of sequence (i) or (ii) encoding the sequence of SEQ ID NO: 8 and the sequence of SEQ ID NO:9, wherein said sequences of SEO ID NO:8 and SEQ ID NO:9 are separated by about 20 bases, wherein said sequence of SEQ ID NO:8 is 5' to said sequence of SEQ ID NO:9 in said RNA transcript.

3. The construct according to claim 2 wherein said 3' end formation directing sequence consists of a sequence: i) defined by position 100 to position 347 of SEQ ID NO:18 or ii) position 1 to position 223 of SEQ ID NO:18, or portion of sequence (i) or sequence (ii) that includes the sequence defined by position 147 to position 186 of SEQ ID NO:18.

4. The construct according to claim 2 wherein said 3' end formation directing sequence consists of a sequence encoding the sequence of SEQ ID NO:8 and sequence of SEQ ID NO:9 separated by about 20 bases, wherein said sequence of SEQ ID NO:8 is 5' to said sequence of SEQ ID NO:9 in said RNA transcript.

5. The construct according to claim 2 wherein said 3' end formation directing sequence consists of a sequence defined by position 147 to position 186 of SEQ ID NO:18.

6. A host cell transformed with the construct according to claim 2.

7. The cell according to claim 6 wherein said cell is infected with a replicating poxvirus.

8. A method of directing cleavage of an RNA transcript comprising culturing the cell according to claim 7 under conditions such that said encoding sequences are transcribed so that a transcript of said non-A-type inclusion protein encoding sequence is produced and the 3' end thereof is specifically cleaved.

9. A DNA construct comprising a first component and a second component, said first component consisting of a non-A-type inclusion protein-encoding sequence and, 3' thereto, a sequence that directs 3' end formation of an RNA transcript of said non-A-type inclusion protein-encoding sequence, wherein said 3' end formation directing sequence consists of a sequence: i) defined by position 100 to position 347 of SEQ ID NO:18 or ii) position 1 to position 223 of SEQ ID NO:18, or portions of sequence (i) or (ii) encoding the sequence of SEQ ID NO:8 and the sequence of SEQ ID NO:9, wherein said sequences of SEQ ID NO:8 and SEQ ID NO:9 are separated by about 20 bases, wherein said sequence of SEQ ID NO: 8 is 5' to said sequence of SEQ ID NO:9 in said RNA transcript, and said second component comprising a promoter, said promoter being operably linked to said non-A-type inclusion protein-encoding sequence.

* * * * *

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CGGGATCCGT AACGAAACAT CCATCG                                                    26

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCCTGCAGGC GGCCGCTTTT TTTTTTTTT TTT                                             33

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GCTCTAGAGA GTTAAATGCC TCAGACGC                                                  28

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCCTGCAGGC GGC                                                                  13

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:5:

CACAAAAGAU UUUAUAAAA AAAAAAAAA AA                                               32

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:6:

CACAAAAGAU UUUAUAUUAA AAAAAAAAA AAAAA                                           36

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:7:

CACAAAGAU UUUAUC       16

( 2 ) INFORMATION FOR SEQ ID NO:8:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:8:

UUUAUCCGAU       10

( 2 ) INFORMATION FOR SEQ ID NO:9:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:9:

CGGAUUUGAA       10

( 2 ) INFORMATION FOR SEQ ID NO:10:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:10:

CACAAAGAU UUUAUCCGAU AAUUCUUCAU CAGACAAUUU CGGAUUUGAA UGC       53

( 2 ) INFORMATION FOR SEQ ID NO:11:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

TAAAATAGGC TATT       14

( 2 ) INFORMATION FOR SEQ ID NO:12:

( i ) SEQUENCE CHARACTERISTICS:
        ( A ) LENGTH: 14 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

TTATCGGATA AAAT 14

(2) INFORMATION FOR SEQ ID NO:13:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

TATCGGATAA AATC 14

(2) INFORMATION FOR SEQ ID NO:14:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

TTATCGGATA AAAT 14

(2) INFORMATION FOR SEQ ID NO:15:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: RNA (genomic)

(xi) SEQUENCE DESCRIPTION: SEQ ID NO:15:

CACAAAAGAU UUUAUCCGAU AAUUCUUCAU 30

(2) INFORMATION FOR SEQ ID NO:16:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: RNA (genomic)

(xi) SEQUENCE DESCRIPTION: SEQ ID NO:16:

CACAAAAGAU UUUAUAAAAA AAAAAAAAA 30

(2) INFORMATION FOR SEQ ID NO:17:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:17:

CAAAAGATTT TATCCGA 17

( 2 ) INFORMATION FOR SEQ ID NO:18:

( i ) SEQUENCE CHARACTERISTICS:
    ( A ) LENGTH: 347 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:18:

| | | | | | |
|---|---|---|---|---|---|
| AGCTTCGTCT | TTTTACCTCT | ACATCTAACG | GTTGCCTTGT | CCTGAGTTAA | ATGCCTCAGA | 60 |
| CGCAAGTAAT | AAATTGGTCC | AAAAATACT | TTGGATGCAT | AAGGCTTATC | CGTTTCAGGA | 120 |
| TCATAGAGAA | TCTTTTCACA | AAAGATTTTA | TCCGATAATT | CTTCATCAGA | CAATTTCGGA | 180 |
| TTTGAATGCT | CATAACATTG | TTTAGCGAAT | TGCATATATG | TATCGATGGA | TGTTTCGTTA | 240 |
| CTACTAGGAA | AACAGACAGG | TCGGTTTTCT | CCCTTATTGT | TGTACGGCTT | AGCAGAATAT | 300 |
| GCGGCTGTTA | AAATAACTTC | TATCAACATA | GATATAGTTT | TTCTAGA | | 347 |

( 2 ) INFORMATION FOR SEQ ID NO:19:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:19:

CACAAAAGAU UUUAUCCGAU AAUUCUUCAU CAGACAAUUU CGGAUUUGAA UGC 53

( 2 ) INFORMATION FOR SEQ ID NO:20:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:20:

AAGAUUUUAU CCGAUAAUUC UUCAUCAGAC AAUUCGGAU UUGAAUGC 48

( 2 ) INFORMATION FOR SEQ ID NO:21:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:21:

UUUAUCCGAU AAUUCUUCAU CAGACAAUUU CGGAUUUGAA UGC 43

( 2 ) INFORMATION FOR SEQ ID NO:22:

( i ) SEQUENCE CHARACTERISTICS:
    ( A ) LENGTH: 50 base pairs (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:22:

CACAAAAGAU UUUAUCCGAU AAUUCUUCAU CAGACAAUUU CGGAUUUGAA    50

(2) INFORMATION FOR SEQ ID NO:23:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:23:

CACAAAAGAU UUUAUCCGAU AAUUCUUCAU CAGACAAUUU CGGAU    45

(2) INFORMATION FOR SEQ ID NO:24:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:24:

CACAAAAGAU UUUAUCCGAU AAUUCUUCAU CAGACAAUUU    40

(2) INFORMATION FOR SEQ ID NO:25:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:25:

CACAAAAGAU UUUAUGUACA AAUUCUUCAU CAGACAAUUU CGGAUUUGAA UGC    53

(2) INFORMATION FOR SEQ ID NO:26:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:26:

CACAAAAGAU UUUAUCCGAU GUACAUUCAU CAGACAAUUU CGGAUUUGAA UGC    53

(2) INFORMATION FOR SEQ ID NO:27:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: RNA (genomic)

( x i ) SEQUENCE DESCRIPTION: SEQ ID NO:27:

CACAAAAGAU UUUAUCCGAU AAUUCGUACA CAGACAAUUU CGGAUUUGAA UGC  53

( 2 ) INFORMATION FOR SEQ ID NO:28:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:28:

CACAAAAGAU UUUAUCCGAU AAUUCUUCAU GUACAAAUUU CGGAUUUGAA UGC  53

( 2 ) INFORMATION FOR SEQ ID NO:29:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:29:

CACAAAAGAU UUUAUCCGAU AAUUCUUCAU CAGACGUACA CGGAUUUGAA UGC  53

( 2 ) INFORMATION FOR SEQ ID NO:30:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:30:

CACAAAAGAU UUUAUCCGAU AAUUCUUCAU CAGACAAUUU GUACAUUGAA UGC  53

( 2 ) INFORMATION FOR SEQ ID NO:31:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:31:

UUUAUCCGAU  10

( 2 ) INFORMATION FOR SEQ ID NO:32:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:32:

CGGAUUUGAA  10

( 2 ) INFORMATION FOR SEQ ID NO:33:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:33:

CACAAAAGAU UUUAUCCGAU AAUUCUUCAU CAGACAAUUU CGGAUUUGAA UGC     53

( 2 ) INFORMATION FOR SEQ ID NO:34:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:34:

CACAAAAGAU UUUAUAAAAA AAAAAAAAAA     30

( 2 ) INFORMATION FOR SEQ ID NO:35:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:35:

CACAAAAGAU UUUAUAAAAA AAAAAAAAAA AAA     33

( 2 ) INFORMATION FOR SEQ ID NO:36:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:36:

CACAAAAGAU UUUAUAAAAA AAAAAAAAAA AAAA     34

( 2 ) INFORMATION FOR SEQ ID NO:37:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:37:

CACAAAAGAU UUUAUAAAAA AAAAAAAAAA AAAAA     35

( 2 ) INFORMATION FOR SEQ ID NO:38:

( i ) SEQUENCE CHARACTERISTICS:
        ( A ) LENGTH: 37 base pairs 5,578,468

33

34

-continued ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:38:

CACAAAAGAU UUUAUAAAAA AAAAAAAAA AAAAAA                                    37

( 2 ) INFORMATION FOR SEQ ID NO:39:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:39:

CACAAAAGAU UUUAUAAAAA AAAAAAAAA AAAAAAAAA A                               41

( 2 ) INFORMATION FOR SEQ ID NO:40:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:40:

CACAAAAGAU UUUAUAAAAA AAAAAAAAA AAAAAAAAA AAAA                            44

( 2 ) INFORMATION FOR SEQ ID NO:41:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:41:

CACAAAAGAU UUUAUAAAAA AAAAAAAAA AAAAAAAAA AAAAAAAAA AAAAA                 55

( 2 ) INFORMATION FOR SEQ ID NO:42:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:42:

CAAAACAAAA AAAAAAAAA AAAAA                                                25

( 2 ) INFORMATION FOR SEQ ID NO:43:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: RNA (genomic)

-continued ( x i ) SEQUENCE DESCRIPTION: SEQ ID NO:43:

CACAAAAGAU UUUAUAAAAA AAAAAAAAAA AAAAAA 36

( 2 ) INFORMATION FOR SEQ ID NO:44:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: RNA (genomic)

( x i ) SEQUENCE DESCRIPTION: SEQ ID NO:44:

CAAAAAAAAA AAAAAAAAAA AAAAAAAAAA AAAAAAA 37